US012559709B2

(12) United States Patent
Mathys et al.

(10) Patent No.: US 12,559,709 B2
(45) Date of Patent: Feb. 24, 2026

(54) MODIFIED TREATMENT CHAMBER FOR TREATING CELLS

(71) Applicant: Bühler AG, Uzwil (CH)

(72) Inventors: Alexander Mathys, Zurich (CH);
Leandro Buchmann, Winterthur (CH);
Erika Sylvie Georget, Zurich (CH);
Jana Carmen Bünder, Baldegg (CH)

(73) Assignee: Bühler AG, Uzwil (SE)

( * ) Notice: Subject to any disclaimer, the term of this patent is extended or adjusted under 35 U.S.C. 154(b) by 685 days.

(21) Appl. No.: 17/797,866

(22) PCT Filed: Feb. 4, 2021

(86) PCT No.: PCT/EP2021/052674
§ 371 (c)(1),
(2) Date: Aug. 5, 2022

(87) PCT Pub. No.: WO2021/156373
PCT Pub. Date: Aug. 12, 2021

(65) Prior Publication Data
US 2023/0067450 A1 Mar. 2, 2023

(30) Foreign Application Priority Data
Feb. 7, 2020 (EP) .................................... 20156009

(51) Int. Cl.
*C12M 1/42* (2006.01)
*C12M 1/00* (2006.01)
*C12N 13/00* (2006.01)

(52) U.S. Cl.
CPC ............ *C12M 35/02* (2013.01); *C12M 47/06* (2013.01); *C12N 13/00* (2013.01)

(58) Field of Classification Search
None
See application file for complete search history.

(56) References Cited

U.S. PATENT DOCUMENTS

| | | | |
|---|---|---|---|
| 4,946,793 A | 8/1990 | Marshall, III | |
| 5,656,926 A | 8/1997 | Ragsdale | |
| 6,074,605 A * | 6/2000 | Meserol .................. | C12M 35/02 |
| | | | 435/173.6 |
| 6,749,736 B1 | 6/2004 | Fuhr et al. | |
| 10,421,956 B2 | 9/2019 | Caiafa et al. | |
| 2003/0050591 A1 | 3/2003 | Patrick | |
| 2008/0076144 A1 | 3/2008 | Ragsdale | |
| 2008/0106238 A1 | 5/2008 | Ragsdale | |
| 2009/0155877 A1 | 6/2009 | Iliescu et al. | |
| 2011/0107655 A1 | 5/2011 | Kempkes et al. | |
| 2012/0067639 A1 | 3/2012 | Altrogge et al. | |
| 2014/0030696 A1 | 1/2014 | Luscher et al. | |
| 2014/0324147 A1 * | 10/2014 | Wagner .............. | A61N 1/36046 |
| | | | 607/141 |
| 2018/0051243 A1 | 2/2018 | Hogan et al. | |

| | | | |
|---|---|---|---|
| 2019/0119624 A1 | 4/2019 | Tandon et al. | |
| 2019/0168222 A1* | 6/2019 | Kojima ............. | B01L 3/502738 |
| 2019/0264160 A1 | 8/2019 | Antonio et al. | |
| 2019/0307500 A1 | 10/2019 | Byrd et al. | |

FOREIGN PATENT DOCUMENTS

| | | |
|---|---|---|
| CN | 205188309 U | 4/2016 |
| CN | 110527624 A | 12/2019 |
| DE | 10127247 A1 | 12/2002 |
| EP | 0283700 A2 | 9/1988 |
| EP | 2308969 A1 | 4/2011 |
| JP | 63-084481 A | 4/1988 |
| JP | H01-262786 A | 10/1989 |
| KR | 1020130129812 | 11/2013 |
| WO | 03/050546 A2 | 6/2003 |
| WO | 2005/032646 A2 | 4/2005 |
| WO | 20017/059162 A2 | 5/2007 |
| WO | 2016/164930 A1 | 10/2016 |

OTHER PUBLICATIONS

Buchmann Leandro and Alexander Mathys, "Perspective on Pulsed Electric Field Treatment in the Bio-based Industry", Frontiers in Bioengineering and Biotechnology, Oct. 2019, vol. 7, 7 pages, See pp. 1, 3 & 14.
European Search Report Corresponding to 20156005.9 mailed Jul. 13, 2020.
International Search Report Corresponding to PCT/EP2021/052665 mailed Apr. 21, 2021.
Written Opinion Corresponding to PCT/EP2021/052665 mailed Apr. 21, 2021.
European Search Report for Application No. 20156006.7 dated Aug. 19, 2020.
International Search Report Corresponding to PCT/EP2021/052667 mailed Nov. 5, 2021.
Written Opinion Corresponding to PCT/EP2021/052667 mailed Nov. 5, 2021.
European Search Report Corresponding to 20156008.3 mailed May 19, 2020.
International Search Report and Written Opinion of the International Searching Authority for International Application No. PCT/EP2021/052674 dated Nov. 11, 2021, 11 pages.
International Search Report Corresponding to PCT/EP2021/052673 mailed Apr. 29, 2021.
Written Opinion Corresponding to PCT/EP2021/052673 mailed Apr. 29, 2021.
European Search Report Corresponding to 20156009.1 mailed Jul. 13, 2020.

(Continued)

*Primary Examiner* — Michelle F. Paguio Frising
(74) *Attorney, Agent, or Firm* — Finch & Maloney PLLC

(57) ABSTRACT

The present invention is related to a treatment unit (3) having an inlet (3a) and an outlet (3b), and a treatment space (4) being formed inside the treatment unit (3) such that it can be penetrated by electric pulses, said treatment space (4) being fluidly connected with the inlet (3a) and the outlet (3b), wherein at least a portion of an inner side face of the treatment space (4) is curved. The present invention is furthermore related to a device comprising such a treatment unit and to a method to be performed with said device, and wherein the inlet (3a) is formed in a top face of the treatment unit (3), and the outlet (3b) is formed in a bottom face of the treatment unit (3).

16 Claims, 3 Drawing Sheets

(56)           References Cited

OTHER PUBLICATIONS

International Search Report Corresponding to PCT/EP2021/052674 mailed Nov. 11, 2021.
Written Opinion Corresponding to PCT/EP2021/052674 mailed Nov. 11, 2021.
New Zealand Patent Examination Report Corresponding to 790572 mailed Oct. 9, 2024, 6 pages.
Korean Office Action Corresponding to 10-2022-7027861 mailed Sep. 20, 2024.
New Zealand Office Acton Corresponding to 490571 dated Mar. 26, 2024.
V. Novickij et al., "Pulsed Electromagnetic Field Assisten in vitro Electroporation: A Pilot Study" Scientific Reports, 6:33537, Sep. 16, 2016.
Chinese Office Action Corresponding to 202180011784.6 mailed Jun. 28, 2025.

* cited by examiner

MODIFIED TREATMENT CHAMBER FOR TREATING CELLS

TECHNICAL FIELD

The present invention relates to a treatment unit for a device for medical, environmental, food applications, and bio-based industries (including yeast, lactobacilli, algae, and cell tissue production systems, in particular including targeted inactivation, the extraction of bioactive compounds, and the stimulation of cell growth and/or cellular compounds.

BACKGROUND ART

It is known that prokaryotic and eukaryotic cells are influenced by the action of electric fields. Stimulation of cell growth, as well as cell death, inactivation of microorganisms, or specific extraction of cell constituents can occur, depending on the applied electric field strength (e.g. Buchmann L and Mathys A (2019), Perspective on Pulsed Electric Field Treatment in the Bio-based Industry, Front. Bioeng. Biotechnol. 7:265, doi: 10.3389/fbioe.2019.00265).

EP-2 308 969 B1 describes a PEF (pulsed electric field) method where a cell material suspended in an electrically conductive liquid, the cell material being positioned between two electrodes, by exposure of 1 to 100 electric field strength pulses, such that a voltage increase takes place between the two electrodes of 10% to 90% of a target voltage of the electric field strength pulses within a period of 0.1 to 100 ns, the electric field strength pulses have a pulse duration of 5 ns to 5000 ns, and the electric field strength pulses, upon reaching the target voltage, have an electric field strength of 0.5 kV/cm to 50 kV/cm, showed an accelerated cell proliferation and/or increased cell constituents.

In the device for treating cell material used in EP 2 308 969 B1, an electroporation cuvette having the suspension of cell material described above was continuously pumped through an arrangement of two electrodes and exposed to an electric field in an electrically conductive liquid (paragraph [0020] of EP-2 308 969 B1).

Under these conditions, a flow profile is formed between the wall and the center of the vessel, which may result in deviations with respect to the process conditions over the vessel diameter. This is a problem since influencing the cell proliferation as described above depends on the accurate maintenance of the process conditions. With the device of EP-2 308 969 B1, it is not possible to obtain homogeneous process conditions in the entire reaction vessel and therefore also no homogeneously influenced cell material.

SUMMARY OF THE INVENTION

It was the object of the present invention to overcome the above problems of the prior art and to provide a device that overcomes difficulties involved with currently available PEF equipment in order to obtain homogenous and controllable flow and electric field profiles.

The above object is achieved by the present invention as defined in the claims.

In detail, the present invention relates to a treatment unit having an inlet and an outlet, and a treatment space being formed inside the treatment unit such that it can be penetrated by electric pulses and an electric field resulting therefrom, said treatment space being fluidly connected with the inlet and the outlet, characterized in that at least a portion of an inner side face of the treatment space is non-planar, preferably curved, and wherein the inlet is formed in a top face of the treatment unit, and the outlet is formed in a bottom face of the treatment unit.

The present invention is also related to a device comprising a unit for generating and emitting electric pulses, wherein said device furthermore comprises a treatment unit according to the present invention.

BRIEF DESCRIPTION OF DRAWINGS

The present invention is explained below by way of non-limiting examples and figures. Shown are.

DETAILED DESCRIPTION OF THE INVENTION

Figure 1:
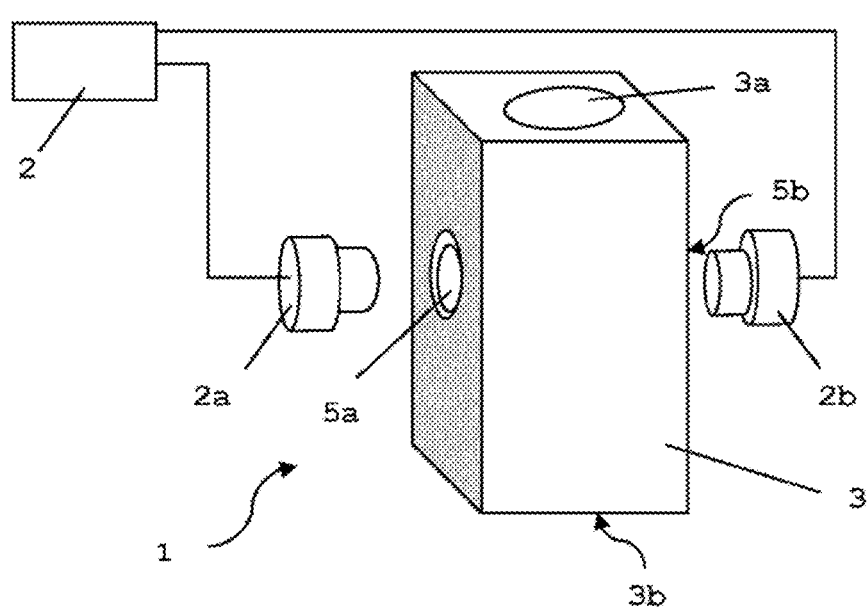
FIG. 1 a schematic representation of an embodiment of the device of the present invention FIG. 2 a schematic representation of the treatment unit of the embodiment of the device of the present invention according to FIG. 1

According to the present invention, it has been found that a more homogeneous treatment is possible in a treatment space that has an inner side face with at least a portion thereof being non-planar. For example, said portion of said inner side face may be curved, triangular, buffled or may have a saw-tooth shape. A curved portion of said inner side face is preferred. The flow of a fluid protruding through said treatment space is thereby significantly homogenized in a zone where the electric field is applied, and as a result treatment of a material flowing through said treatment space, by means of electric pulses, is significantly more homogenous than in a treatment space having plain (i.e. not curved) side faces.

According to the present invention, the inner portion of the treatment space, i.e. not the portions thereof which are in direct vicinity to the non-planar portion(s) of said inner side face(s), are subjected to electric pulses and to an electric field generated therefrom.

According to the present invention, the device is suitable for medical, environmental, food applications, and bio-based industries (including yeast, lactobacilli, algae, and cell tissue production systems, in particular including targeted inactivation, the extraction of bioactive compounds, and the stimulation of cell growth and/or cellular compounds. These applications are described in Buchmann L and Mathys A (2019), Perspective on Pulsed Electric Field Treatment in the Bio-based Industry, Front. Bioeng. Biotechnol. 7:265, doi: 10.3389/fbioe.2019.00265. According to the present invention, electric pulses are applied to a cell material located in the treatment space of a treatment unit while it passes through the treatment space. As a result, the cell material is subjected to the electric pulses and treated.

According to the present invention, basically any material composed of at least one cell, that is, both eukaryotic and prokaryotic cells, can be used as the cell material to be treated. The cell material can be unicellular or multicellular organisms. Examples would be bacteria, yeasts, microalgae, plant cells, and fungal cells or their spores, mycelia, seeds or seedlings and somatic animal cells. Furthermore, multicellular tissues such as meristems in plants and epithelial or connective tissue in humans or animals can be treated.

The cell material is usually (but not necessarily) isolated, purified and/or sterilized in a known manner before being treated according to the invention. Preferably, the cell material can already be propagated in a known manner in suitable and known culture media to a desired degree before the treatment according to the invention.

The cell material is preferably suspended in an electrically conductive liquid prior to the treatment according to the invention. Electrically conductive liquids are well known. According to the invention, it is necessary to use electrically conductive liquids which have no adverse effects on cell viability, that is, in particular, are non-toxic. According to the invention, water is preferably used as the electrically conductive liquid, wherein the water can be adjusted to a desired pH value by means of suitable and known additives. According to the invention, a pH value in the range of 6.0 to 14.0, preferably 7 to 12 is preferred.

According to the present invention, the suspensions described above can be prepared in a conventional manner and stored until treatment. However, the suspensions can also be provided immediately before the treatment according to the invention.

The cell material or a suspension containing the cell material is passed through the inlet of a treatment unit into a treatment space which is located inside the treatment unit.

The inlet of the treatment unit is preferably connected to a device in which the cell material or a suspension containing the cell material is located. For example, conventional pipelines can be provided for this connection.

Preferably, a shut-off unit such as a valve or a lock is provided in or at the inlet or alternatively in the connection described above in order to be able to control the introduction of the cell material or the suspension containing the cell material into the treatment unit.

According to a preferred embodiment of the present invention, the inlet comprises a nozzle or the inlet constitutes a nozzle. It is possible to use nozzles which can conventionally be used for introducing a medium into a container or defined space. Such nozzles are known.

With this embodiment, the speed at which the cell material or a suspension containing the cell material is introduced into the treatment unit can be adjusted in a targeted manner. The residence time of the cell material in the electric field applied to the treatment space of the treatment unit can thereby be adjusted.

The treatment unit into which the cell material to be treated is introduced through the inlet described above, is limited with respect to its shape, structure and dimensions only in that applied electric pulses and an electric field resulting therefrom field can sufficiently penetrate the treatment unit to achieve the desired treatment of the cell material in the treatment unit. According to the invention, the treatment unit is preferably a container made of a metallic material or a plastic material (such as polyethylene terephthalate).

The treatment unit can have any geometric shape. Preferably, the treatment unit is a cuboid or cylindrical body.

A treatment space is provided within the treatment unit, through which treatment space the cell material passes and is thereby treated with electric pulses.

The treatment space can have any geometric shape, but preferably has a cuboid shape. According to a very preferred embodiment of the present invention, said treatment space is positioned in the centre of the treatment unit. Especially preferred the treatment unit is a solid body, and the treatment space is a cavity within said treatment unit, preferably in the centre of the treatment unit.

As described above, the treatment unit comprises an inlet and an outlet. The treatment space within the treatment unit is fluidly connected with the inlet and the outlet of the treatment unit.

According to the present invention, the inlet is formed in a top face of the treatment unit, and the outlet is formed in a bottom face of the treatment unit. Thus, the material flows downwardly through the device of the invention, by means of the gravitational force.

The fluid connection of inlet, treatment space and outlet can be realized by providing conduits such as pipes that protrude from the inlet to the treatment space, and from the treatment space to the outlet. According to a preferred embodiment of the present invention where the treatment unit is a solid body, and the treatment space is a cavity within the treatment unit, the fluid connection of inlet, treatment space and outlet is realized by respective cavities in the treatment unit that protrude from the inlet to the treatment space, and from the treatment space to the outlet.

The fluid connection of inlet, treatment space and outlet can have a uniform shape, such as a cylindrical pipe or cavity with a uniform diameter. It is also possible that the shape of the fluid connection of inlet, treatment space and outlet varies over its length. For example, at least a part of the fluid connection may have a funnel-shaped form. For example, the fluid connection from the inlet to the treatment space may partially have a funnel-shaped form with an opening size decreasing from the inlet to the treatment space, so that the material may be advantageously guided into the treatment space. Likewise, the fluid connection from the treatment space to the outlet may partially have a funnel-shaped form with an opening size increasing from the treatment space to the outlet, so that the material may be advantageously guided to the outlet.

It is the important feature of the present invention that at least a portion of an inner side face of the treatment space is curved. In other words, the treatment space does not exhibit exclusively fully planar inner side faces, but rather at least partially side faces that influence the flow characteristics of the material protruding through the treatment space.

It is preferred that said at least a portion of an inner side face of the treatment space has a regular surface shape. Especially preferred, said inner side face of the treatment space has a sinusoidal shape, at least over a portion thereof.

According to the present invention, a preferred design of the treatment space is such that two side surfaces of the treatment space which lie opposite to each other are curved, and preferably have a sinusoidal shape, over at least 50%, preferably at least 75% and most preferably 100% of their respective heights. Especially preferable is a sinusoidal shape with an amplitude in the range from 5 to 20%, preferably 10 to 15%, of the width of the treatment space, and a wavelength in the range from 50 to 80%, preferably 60 to 70% of the height of the treatment space. So, for example, for a treatment space having a dimension of 24×5×5 mm, a preferred curvature would have a wavelength of 13 mm (i.e. about 66.67% of the height of the treatment space) and an amplitude of 0.67 mm (i.e. about 13.4% of the width of the treatment space).

According to another preferred embodiment of the present invention, there are provided two side surfaces of the treatment space which lie opposite to each other and have a sinusoidal shape such that there is a phase shift of 180° C. between the two side surfaces.

According to an especially preferred embodiment of the present invention, at least one, preferably two side faces of a cuboid treatment space have a curved, preferably sinusoidal shape over the entire height. Especially preferred, these two side faces of the cuboid treatment space lie opposite to each other.

With the above described design of the treatment space, the flow of a material through the treatment space becomes more homogenous due to flow modifications outside the region of the treatment zone where electric pulses are applied. Accordingly, there is less difference between the flow (residence time) of the material in the middle of the treatment space and the flow of the material in vicinity of the side surfaces of the treatment space. Accordingly, electric pulses emitted through the treatment space, and an electric field resulting therefrom, contact a material with more homogeneous characteristics and thus result in a more homogeneous treatment of said material.

The electric pulses to penetrate the treatment space are generated and emitted by electrodes, preferably two electrodes, which are positioned at the treatment unit such that the electric pulses emitted by said electrodes, and thus the electric field resulting therefrom, may sufficiently penetrate the treatment space and thus enable adequate treatment of the material in the treatment space. Alternatively, two plates of a capacitor may be used for this purpose.

According to a preferred embodiment of the present invention, in the region of the treatment space there are provided means for positioning electrodes, or plates of a capacitor, for providing said electric pulses to the treatment space. Those means may be any known component enabling adequate and secure fixation of the electrodes or plates at the treatment unit. For example, fixation tools such as clamping tools may be provided at side faces, preferably opposite side faces, of the treatment unit, so that the electrodes or plates may be securely fixed at the side surfaces of the treatment unit.

According to a very preferred embodiment of the present invention, the means for positioning electrodes are openings in the side faces preferably opposite side faces, of the treatment unit into which electrodes may be inserted. These openings have a size allowing insertion of conventional electrodes and securing the inserted electrodes at place. These openings preferably are located in the vicinity of the treatment space in the treatment unit.

For example, the means may be blind bores in side faces of the treatment unit, which is preferably a solid body. In a preferred embodiment, blind bores are provided in two side faces of the treatment unit opposite to each other. Preferably, these blind bores are located in the vicinity of the treatment space in the treatment unit. It is very preferred that the blind bores have such a depth that their proximal face with respect to the treatment space lies close to a side face of the treatment space. Especially preferred, a side face of the treatment space forms the end face of a blind bore.

According to a preferred embodiment, the blind bores may be tapered from the outside to the inside end, i.e. the opening size of the blind bore decreases from the outside to the inside. This allows secure fixation of an electrode inserted into said blind bore.

In order to not disturb the penetration of electric pulses generated and emitted by said electrodes, preferably the inner face of the blind bores comprises a slit, which preferably is arranged in the centre of the inner face of the blind bore. At the position of the slit, the separating wall between the blind bore and the treatment space is thus thinner. The exact extension of the slit is to be chosen by a skilled person that the remaining side face of the treatment space withstands the flow conditions during the treatment period.

According to a further preferred embodiment, the blind bores (or more generally the means for positioning the electrodes) project towards plain side faces of the treatment space. In other words, according to this embodiment side faces of the treatment space that have a curved inner portion do not lie in vicinity of the electrodes generating and emitting electric pulses.

The outlet of the treatment unit is preferably connected to a device in which the cell material or a suspension containing the cell material can be stored. For example, conventional pipelines can be provided for this connection.

Preferably, a shut-off unit such as a valve or a lock is provided in or at the outlet or alternatively in the connection described above in order to be able to control the outflow of the cell material or the suspension containing the cell material out of the treatment unit.

The treatment process of the present invention may be performed continuously or batch-wise. In the latter case, the treatment unit may be emptied before another treatment cycle is started, Optionally, a sterilization/sanitization step may be performed prior to the start of another treatment cycle. Known sterilization/sanitization processes such as steam-based processes can be used in accordance with the present invention.

The present invention is also related to a device, comprising a unit for generating and emitting electric pulses and a treatment unit as described above.

Units for generating and emitting electric pulses are well known. According to the present invention, devices which can generate electrical impulses as described below are preferred.

Such devices are known. By way of example, cable pulse generators, semiconductor-based pulse generators, or relaxation oscillators can be mentioned.

The generated electric pulses are emitted into the treatment space. This is preferably done by two or more electrodes or plates of a capacitor arranged parallel to each other, which are arranged opposite each another having a distance suitable for the generation of electric pulses. Such arrangements are well known and need not be explained in detail here.

According to a preferred embodiment of the present invention, two electrodes or plates of a capacitor are arranged perpendicularly to the direction of movement of the material through the treatment space.

The electric field to be applied to the treatment space must be characterized such that it provides for the desired effect, e.g. that it stimulates the growth of the treated cells. Corresponding electric fields are known from the prior art, for example from EP-2 308 969 B1. According to the present invention, an electric field generated from such electric pulses can be used, such that a voltage increase takes place between the two electrodes or plates of a capacitor of the device of 10% to 90% of a target voltage of the electric pulses within a period of 0.1 to 1000 ns, the electric pulses have a pulse duration of 5 ns to 50000 ns, and the electric pulses, upon reaching the target voltage, have an electric field strength of 0.5 kV/cm to 100 kV/cm.

The present invention is also related to a method for treating cells for targeted inactivation, the extraction of bioactive compounds, and the stimulation of cell growth and/or cellular compounds, performed in a device as described herein, comprising the steps a) applying electric pulses to a treatment space in a
      treatment unit, b) introducing cell material through an inlet of the treatment unit into the treatment space, c) passing of the cell material through the treatment space and the electric pulses penetrating the treatment space to an outlet of the treatment unit.

The method can be performed as already described above.

As stated above, it is preferred that the cell material is provided as a suspension in an electrically conductive liquid.

As stated above, it is further preferred that an electric field is applied with such electric pulses, so that a voltage increase takes place between the two electrodes or plates of a capacitor of the device of 10% to 90% of a target voltage of the electric pulses within a period of 0.1 to 1000 ns, the electric pulses have a pulse duration of 5 ns to 50000 ns, and the electric pulses, upon reaching the target voltage, have an electric field strength of 0.5 kV/cm to 100 kV/cm.

As stated above, the treatment process of the present invention may be performed continuously or batch-wise. In the latter case, the treatment unit may be emptied before another treatment cycle is started. Optionally, a sterilization/sanitization step may be performed prior to the start of another treatment cycle. Known sterilization/sanitization processes such as steam-based processes can be used in accordance with the present invention.

The present invention further relates to the use of the device according to the present invention described here for medical, environmental, food applications, and bio-based industries (including yeast, bacteria, microalgae, as well as plant or animal cells and cell tissue production systems, in particular targeting inactivation, the extraction of bioactive compounds, and/or the stimulation of cell growth and/or cellular compounds. These applications are described in Buchmann L and Mathys A (2019), Perspective on Pulsed Electric Field Treatment in the Bio-based Industry, Front. Bioeng. Biotechnol. 7:265, doi: 10.3389/fbioe. 2019.00265.

MODES FOR CARRYING OUT THE INVENTION

FIG. 1 shows a schematic representation of an embodiment of the device (1) of the present invention.

The device has a unit (2) for generating and emitting electric pulses, for example, a pulse generator. The unit (2) is electrically connected to two electrodes (2a, 2b). A treatment unit (3) is located between the electrodes (2a, 2b). On a treatment space (4) within said treatment unit (3) (see FIG. 2), electric pulses generated by the unit (2) are applied. The electrodes (2a, 2b) are arranged perpendicularly to the direction of movement of material moving through the treatment unit (3). The material enters the treatment unit (3) through an inlet (3a) in the top face of the treatment unit (3), and leaves the treatment unit (3) through an outlet (3b) in the bottom face of the treatment unit (3).

In two side faces of the treatment unit (3), there are provided openings (5a, 5b), preferably in the form of blind bores, into which the electrodes (2a, 2b) may be inserted and secured.

Figure 2:
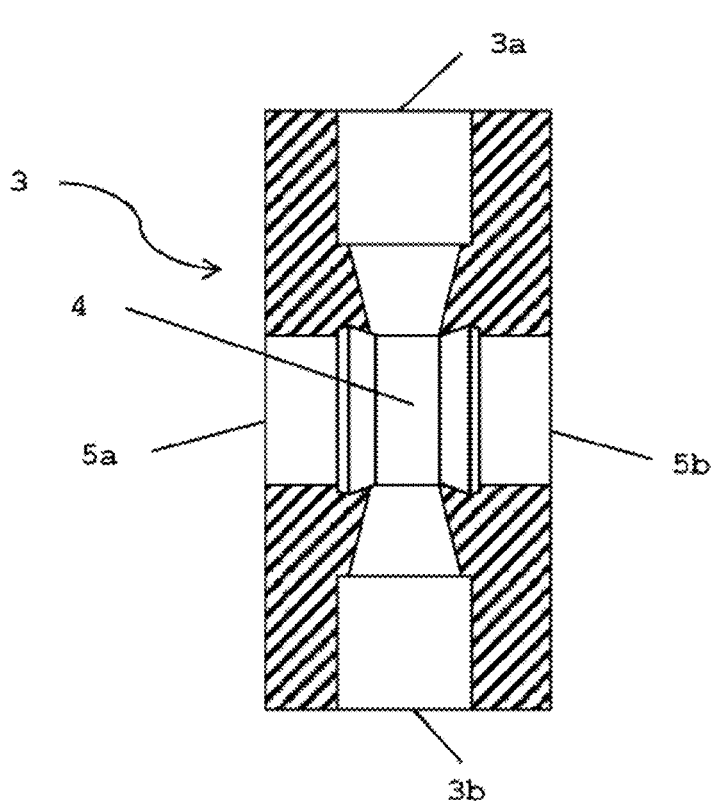

FIG. 2 is a schematic representation of the treatment unit (3) of the embodiment of the device (1) of the present invention according to FIG. 1. Like reference numerals designate the same components as in FIG. 1.

In the embodiment of FIG. 2, the treatment unit (3) is a solid body with a treatment space (4) in the form of a cavity in its center. The inlet (3a) in the top face of the treatment unit (3) is fluidly connected, by means of a conduit, with the treatment space (4). In this embodiment, the fluid connection is funnel-shaped over its lower part discharging into the treatment space (4). The outlet (3b) in the bottom face of the treatment unit (3) is also fluidly connected, by means of a conduit, with the treatment space (4). In this embodiment, the fluid connection is funnel-shaped over it upper part extending from the treatment space (4).

In two side faces of the treatment unit (3), there are provided openings (5a, 5b) in the form of blind bores for insertion of electrodes. These openings are tapered in a region adjacent to the treatment space (4), i.e. they become smaller as they approach the treatment space (4). The side faces of the treatment space (4) adjacent to the openings (5a, 5b) are plain, i.e. they are not curved.

Figure 3A:
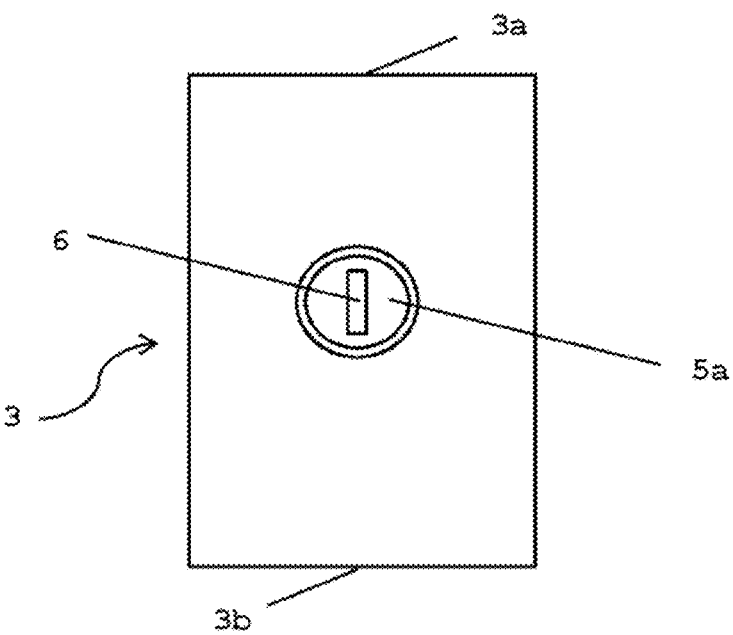
FIG. 3a a side view of the treatment unit of the embodiment of the device of the present invention according to FIG. 1

FIG. 3a is a side view of the treatment unit (3) of the embodiment of the device (1) of the present invention according to FIG. 1. Like reference numerals designate the same components as in FIG. 1.

In FIG. 3a, a side face of the treatment unit (3) is shown in which there is provided an opening (5a) in the form of a blind bore. Said blind bore is tapered in a region adjacent to the treatment space (4, not shown here), i.e. it becomes smaller with increasing depth. In the inner face of the opening (5a), preferably in the center of the inner face, there is provided a slit (6).

Figure 3B:
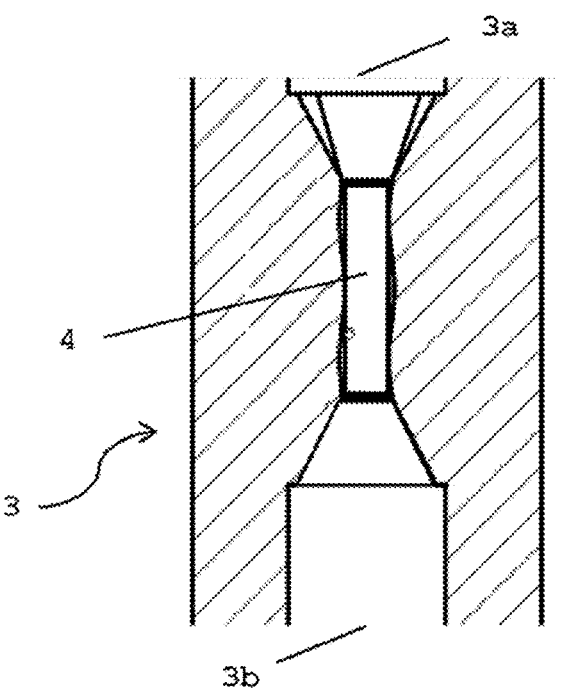
FIG. 3b another schematic representation of the treatment unit of the embodiment of the device of the present invention according to FIG. 1.

FIG. 3b is another schematic representation of the treatment unit (3) of the embodiment of the device (1) of the present invention according to FIG. 1. Like reference numerals designate the same components as in FIG. 1.

As compared to FIG. 2, the treatment unit (3) is turned by 90°. Thus, in FIG. 3b the side faces of the treatment space (4) are shown that are not adjacent to the openings (5a, 5b). These side faces are curved. Here, they have a sinusoidal shape over their entire height.

The invention claimed is:

1. A treatment unit having an inlet and an outlet, and a treatment space being formed inside the treatment unit such that it can be penetrated by electric pulses, said treatment space being fluidly connected with the inlet and the outlet, wherein at least a portion of an inner side face of the treatment space is non-planar, and wherein the inlet is formed in a top face of the treatment unit, and the outlet is formed in a bottom face of the treatment unit, and wherein the flow of a fluid protruding through said treatment space is homogenized in a zone where the electric field is applied.

2. The treatment unit according to claim 1, wherein said portion of the inner side face of the treatment space is curved.

3. The treatment unit according to claim 2, wherein said inner side face of the treatment space has a sinusoidal shape.

4. The treatment unit according to claim 3, wherein at least one side face of the cuboid treatment space has a curved shape over the entire height.

5. The treatment unit according to claim 4, wherein said at least one side face of the cuboid treatment space has a sinusoidal shape over the entire height.

6. The treatment unit according to claim 1, wherein the treatment space has a cuboid shape, with its top face being fluidly connected with the inlet and its bottom face being fluidly connected with the outlet.

7. The treatment unit according to claim 1, wherein in the region of the treatment space there are provided means for positioning electrodes for providing said electric pulses to the treatment space.

8. The treatment unit according to claim 7, wherein the means comprise blind bores in side faces of the treatment unit.

9. The treatment unit according to claim 8, wherein an inner face of the blind bores comprises a slit.

10. The treatment unit according to claim 9, wherein the slit is arranged in the center of the inner face of the blind bores.

11. The treatment unit according to claim 8, wherein the blind bores project towards plain side faces of the treatment space.

12. A device, comprising a unit for generating and emitting electric pulses, wherein said device comprises a treatment unit according to claim 1.

13. The device according to claim 12, wherein the unit for generating and emitting electric pulses comprises two or more electrodes or plates of a capacitor and can generate electric field strength pulses, so that a voltage increase take place between the two or more electrodes of 10% to 90% of a target voltage of the electric field strength pulses within a period of 0.1 to 1000 ns, the electric field strength pulses have a pulse duration of 5 ns to 50000 ns, and the electric field strength pulses, upon reaching the target voltage, have an electric field strength of 0.5 kV/cm to 100 kV/cm.

14. A method for treating cells for targeted inactivation, the extraction of bioactive compounds, and/or the stimulation of cell growth and/or cellular compounds, performed in a device according to claim 12, comprising the steps:

a) introducing cell material through an inlet of a treatment unit into a treatment space;

b) applying electric pulses to the treatment space in the treatment unit; and c) passing the cell material through the treatment space and the electric pulses penetrating the treatment space to an outlet of the treatment unit.

15. The method according to claim 14, wherein the cell material is provided as a suspension in an electrically conductive liquid.

16. The method according to claim 14, wherein an electric field is applied with such electric field strength pulses that a voltage increase takes place between the two electrodes or plates of a capacitor of 10% to 90% of a target voltage of the electric field strength pulses within a period of 0.1 to 1000 ns, the electric field strength pulses have a pulse duration of 5 ns to 50000 ns, and the electric field strength pulses, upon reaching the target voltage, have an electric field strength of 0.5 kV/cm to 100 kV/cm.

* * * * *